United States Patent
Pasquier et al.

(10) Patent No.: US 7,658,771 B2
(45) Date of Patent: *Feb. 9, 2010

(54) COLORING AGENTS FOR KERATIN FIBERS

(75) Inventors: Cécile Pasquier, Marly (CH); Eric Tinguely, Fribourg (CH); Markus Speckbacher, Aschaffenburg (DE); Annik Marguet, Villarsel-le Gibloux (CH); Hans-Jürgen Braun, Ueberstorf (CH)

(73) Assignee: The Procter & Gable Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/393,539

(22) Filed: Feb. 26, 2009

(65) Prior Publication Data
US 2009/0158532 A1    Jun. 25, 2009

Related U.S. Application Data

(63) Continuation of application No. 11/707,371, filed on Feb. 16, 2007, now Pat. No. 7,513,917.

(30) Foreign Application Priority Data

Feb. 18, 2006    (EP)    ................... 06003343

(51) Int. Cl.
*A61Q 5/10* (2006.01)
*C09B 44/00* (2006.01)
(52) U.S. Cl. ............ 8/405; 8/407; 8/437; 8/463; 8/570; 8/571; 8/572; 8/573; 8/574; 8/575; 8/576; 8/587; 534/615
(58) Field of Classification Search ......... 8/405, 8/407, 435, 437, 463, 570, 571, 572, 573, 8/574, 575, 576, 587; 534/615
See application file for complete search history.

(56) References Cited

U.S. PATENT DOCUMENTS

| | | | |
|---|---|---|---|
| 3,578,386 A | 5/1971 | Kalopissis et al. | |
| 4,432,899 A * | 2/1984 | Linhart et al. | 534/615 |
| 5,284,939 A * | 2/1994 | Nicopoulos et al. | 534/582 |
| 7,513,917 B2 * | 4/2009 | Pasquier et al. | 8/405 |

FOREIGN PATENT DOCUMENTS

| | | |
|---|---|---|
| CN | 1445287 | 10/2003 |
| DE | 19618595 A1 | 11/1997 |
| DE | 10118271 A1 | 3/2002 |
| FR | 2782035 A1 | 2/2000 |
| GB | 1162665 A | 8/1969 |
| WO | WO 95/01722 A1 | 1/1995 |

OTHER PUBLICATIONS

International Search Report for PCT/IB2007/050428, Jul. 4, 2007 (6 pages).
Advanced Organic Chemistry—Reactions, Mechanisms and Structure (Jerry March, 5$^{th}$ Edition (2001), pp. 368-375.

* cited by examiner

*Primary Examiner*—Eisa B Elhilo
(74) *Attorney, Agent, or Firm*—Melissa G. Krasovec

(57) ABSTRACT

The present invention relates to agents for coloring keratin fibers which comprise at least one cationic azodye of the general formula (I).

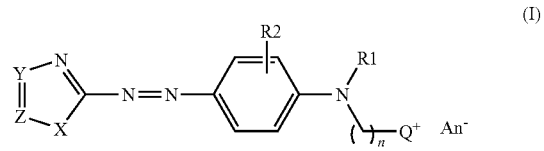

10 Claims, No Drawings

COLORING AGENTS FOR KERATIN FIBERS

CROSS REFERENCE TO RELATED APPLICATIONS

This application is continuation of U.S. application Ser. No. 11/707,371 filed on Feb. 16, 2007 now U.S. Pat. No. 7,513,917.

FIELD OF THE INVENTION

The present invention relates to agents for coloring keratin fibers, such as, for example, wool, furs and, in particular, human hair, comprising cationic azodyes.

BACKGROUND OF THE INVENTION

For the color-changing treatment of keratin fibers two coloring methods usually are used. In the first method, the coloration is produced with so-called oxidative or permanent colorants using a mixture of various developer substances and coupler substances and an oxidizing agent. If required, in this method, so-called direct (nonoxidative) dyes can be added to top off the coloring result or to produce particular color effects. The second method uses exclusively direct dyes, which are applied to the fibers in a suitable carrier mass. This method is easy to use, exceptionally gentle and is characterized by low damage to keratin fibers. The direct dyes used here are subject to a large number of requirements. For example, they have to be acceptable from a toxicological and dermatological point of view and allow the attainment of colorations in the desired intensity, which, inter alia, also requires adequate solubility in water. In addition, good lightfastness, acid fastness and rubbing fastness is required for the colorations achieved.

Compared with oxidative colorations, nonoxidative colorations, however, generally have lower durability and a poorer eveness of color. In addition, direct colorants are generally not able to "lighten" the hair since many direct dyes do not withstand the oxidizing agents required for the lightening and or the required pH of greater than or equal to 9.

WIPO Application Nos. WO 95/01722 A1 and WO 97/20545 A1 disclose colorants which comprise cationic azo dyes, in which the positive charge is delocalised in the conjugated system. Cationic azodyes, in which the cationic charge is localized in a side chain, are known to dye synthetic fibres, as described in European Application No. EP 56578 A1, for example. German Application No. DE 10118271 A1 discloses among others cationic disazodiazole derivatives and their use in hair dyes.

SUMMARY OF THE INVENTION

It has now been found that special cationic azodyes color can dye keratin fibers intensely and durably, are oxidation-stable, and thus can also be used in oxidative coloring systems.

DETAILED DESCRIPTION OF THE INVENTION

The present invention therefore provides:
(a) an agent for the nonoxidative coloring of keratin fibers, in particular human hair;
(b) an agent for the simultaneous lightening and coloring of keratin fibers, in particular human hair, which, besides the dye of the formula (I), comprises an oxidizing agent; and
(c) an oxidative colorant for keratin fibers, in particular human hair, based on at least one oxidation dye precursor;

where the agents (a), (b), and (c) are characterized by comprising at least one azodye of the general formula (I);

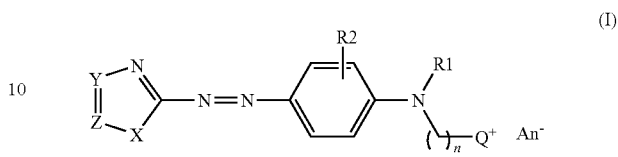

in which
X is oxygen, sulfur, N—R3, C—R4;
Y is C—R5, nitrogen, N—R6, sulfur or oxygen;
Z is C—R7 or nitrogen;
with the proviso that the heterocycle of the formula (I) comprises at least two and at most three heteroatoms, where the heterocycle has at most one sulfur atom or one oxygen atom;
n is an integer from 1 to 6;
R1 is hydrogen, a saturated or unsaturated $(C_1\text{-}C_{12})$-alkyl group, a $(C_1\text{-}C_{12})$-alkyl group substituted by a halogen atom (F, Cl, Br, I), a hydroxy-$(C_2\text{-}C_{12})$-alkyl group, an amino-$(C_1\text{-}C_{12})$-alkyl group, a substituted or unsubstituted phenyl group or a substituted or unsubstituted benzyl group;
R2, R4, R5, and R7 may be identical or different and, independently of one another, are hydrogen, a halogen atom (F, Cl, Br, I), a saturated or unsaturated $(C_1\text{-}C_{12})$-alkyl group, a $(C_1\text{-}C_{12})$-alkyl group substituted by a halogen atom (F, Cl, Br, I), a hydroxyl group, a hydroxy-$(C_1\text{-}C_{12})$-alkyl group, a $(C_1\text{-}C_{12})$-alkoxy group, a $(C_1\text{-}C_{12})$-thioalkyl group, a cyano group, a nitro group, an amino group, a $(C_1\text{-}C_{12})$-alkylamino group, a $(C_1\text{-}C_{12})$-dialkylamino group, a carboxylic acid group, a C(O)O—$(C_1\text{-}C_{12})$-alkyl group, a substituted or unsubstituted C(O)O-phenyl group, a substituted or unsubstituted phenyl group or a naphthyl group, a substituted or unsubstituted heteroaryl group;
or if Y and Z are C—R5 and C—R7, the radical groups R5 and R7, together with the remaining molecule, can form a heterocyclic or carbocyclic, saturated or unsaturated, substituted or unsubstituted ring system;
or if X and Y are C—R4 and C—R5, the radical groups R4 and R5, together with the remaining molecule, can form a heterocyclic or carbocyclic, saturated or unsaturated, substituted or unsubstituted ring system;
R3 and R6 may be identical or different and, independently of one another, are a saturated or unsaturated $(C_1\text{-}C_{12})$-alkyl group, a $(C_1\text{-}C_{12})$-alkyl group substituted by a halogen atom (F, Cl, Br, I), a hydroxy-$(C_2\text{-}C_{12})$-alkyl group, an amino-$(C_1\text{-}C_{12})$-alkyl group, a substituted or unsubstituted phenyl group or a substituted or unsubstituted benzyl group;
Q+ represents a quaternary monoalkylammonium, dialkylammonium or trialkylammonium, where the alkylgroups may be identical or different and, independently of one another, are a saturated or unsaturated $(C_1\text{-}C_{12})$-alkyl group;
with the proviso that when Q+ represents a tri$(C_1\text{-}C_4)$alkylammonium group, and X is sulfur and Y is nitrogen or a CH group, Z is not a C—R5 residue with R5 representing hydrogen, a halogen atom, a nitro group or an alkylgroup;

or Q+ represents a quaternary monoarylammonium, diarylammonium or triarylammonium, where the arylgroups may be identical or different and, independently of one another, are an unsubstituted or substituted phenylgroup;

or Q+ represents a quaternary alkylarylammonium group, where the alkylgroups may be identical or different and, independently of one another, are a saturated or unsaturated $(C_1-C_{12})$-alkyl group, and the arylgroups may be identical or different and, independently of one another, are an unsubstituted or substituted phenylgroup; the anion An—is an organic or inorganic acid anion, such as, for example, halogen anions (chloride, bromide, iodide), sulfate, acetate, formate, propionate, lactate, perchlorate, hexafluorophosphate, tetrafluoroborate or tetraphenylborate.

Among the abovementioned compounds of the formula (I), preference is given to those in which $Q^+$ represents a quaternary trialkylammonium group, where the alkylgroups may be identical or different and, independently of one another, are a saturated or unsaturated $(C_1-C_{12})$-alkyl group;

with the proviso that when Q+ represents a tri$(C_1-C_4)$alkylammonium group, and X is sulfur and Y is nitrogen or a CH group, Z is not a C—R5 residue with R5 representing hydrogen, a halogen atom, a nitro group or an alkylgroup; alkylgroups may be identical or different and, independently of one another, are a saturated or unsaturated $(C_1-C_{12})$-alkyl group and the aryl group a substituted or unsubstituted phenyl group.

Particularly preferred compounds of the general formula (I) are: 2-[{4-[(4,5-dimethyl-1,3-thiazol-2-yl)diazenyl]phenyl}(ethyl)amino]-N,N,N-trimethylethanaminium bromide; 2-[{4-[(4,5-dimethyl-1,3-thiazol-2-yl)diazenyl]-3-methylphenyl}(ethyl)-amino]-N,N,N-trimethylethanaminium bromide; 2-[{3-chloro-4-[(4,5-dimethyl-1,3-thiazol-2-yl)diazenyl]phenyl}(ethyl)amino]-N,N,N-trimethylethanaminium bromide; 2-[{4-[(4-methyl-1,3-thiazol-2-yl)diazenyl]phenyl}(ethyl)amino]-N,N,N-trimethylethanaminium bromide; 2-[{4-[(4-methyl-1,3-thiazol-2-yl)diazenyl]-3-methylphenyl}(ethyl)amino]-N,N,N-trimethylethanaminium bromide; 2-[{3-chloro-4-[(4-methyl-1,3-thiazol-2-yl)diazenyl]phenyl}(ethyl)amino]-N,N,N-trimethylethanaminium bromide; 2-[{4-[1,3-benzothiazol-2-yldiazenyl]phenyl}(ethyl)amino]-N,N,N-trimethylethanaminium bromide; 2-(ethyl{4-[(6-nitro-1,3-benzothiazol-2-yl)diazenyl]phenyl}amino)-N,N,N-trimethylethanaminium bromide; 2-[{4-[(5,6-dinitro-1,3-benzothiazol-2-yl)diazenyl]phenyl}(ethyl)amino]-N,N,N-trimethylethanaminium bromide; 2-[{4-[(4,6-dinitro-1,3-benzothiazol-2-yl)diazenyl]phenyl}(ethyl)amino]-N,N,N-trimethylethanaminium bromide; 2-(ethyl{4-[(4-methyl-6-nitro-1,3-benzothiazol-2-yl)diazenyl]phenyl}amino)-N,N,N-trimethylethanaminium bromide; 2-[{4-[(4-chloro-6-nitro-1,3-benzothiazol-2-yl)diazenyl]-phenyl}(ethyl)amino]-N,N,N-trimethylethanaminium bromide; 2-(ethyl{4-[1H-[1,3]thiazolo[5,4-f]-indazol-6-yl-diazenyl]phenyl}amino)-N,N,N-trimethylethanaminium bromide; 2-[{4-[(5-chloro[1,3]thiazolo[5,4-b]pyridin-2-yl)diazenyl]phenyl}(ethyl)amino]-N,N,N-trimethylethanaminium bromide; 2-[{4-[(5-methoxy[1,3]thiazolo[5,4-b]pyridin-2-yl)diazenyl]-phenyl}(ethyl)amino]-N,N,N-trimethylethanaminium bromide; N,N-diethyl-2-(ethyl{4-[1,3-thiazol-2-yldiazenyl]phenyl}amino)-N-methylethanaminium bromide; N-[2-(ethyl{4-[1,3-thiazol-2-yldiazenyl]phenyl}amino)ethyl]-N,N-dimethylbenzenaminium bromide; 2-(ethyl{4-[1,2,4-thiadiazol-5-yldiazenyl]phenyl}amino)-N,N,N-trimethylethanaminium bromide; 2-(ethyl{4-[(3-phenyl-1,2,4-thiadiazol-5-yl)diazenyl]phenyl}amino)-N,N,N-trimethylethanaminium bromide; 2-[{4-[(3-chloro-1,2,4-thiadiazol-5-yl)diazenyl]phenyl}(ethyl)amino]-N,N,N-trimethylethanaminium bromide; 2-(ethyl{4-[1H-1,2,4-triazol-5-yldiazenyl]phenyl}-amino)-N,N,N-trimethylethanaminium bromide; 1-[2-(ethyl{4-[(1-methyl-1H-imidazol-2-yl)diazenyl]-phenyl}amino)ethyl]-N,N,N-trimethylethanaminium bromide; 1-[2-(ethyl{3-methyl-4-[(1-methyl-1H-imidazol-2-yl)diazenyl]phenyl}amino) ethyl]-N,N,N-trimethylethanaminium bromide and 1-{2-[{3-chloro-4-[(1-methyl-1H-imidazol-2-yl)diazenyl] phenyl}(ethyl)amino]ethyl}-N,N,N-trimethylethanaminium bromide.

The dyes of the formula (I) are present in the colorant according to the invention preferably in an amount of from 0.01% to 10% by weight, in particular from 0.1% to 8% by weight.

To extend the color pallet, the colorant (a) according to the invention can in addition to the dyes of the formula (I), also comprises further known direct synthetic dyes from the group consisting of nitro dyes, azo dyes, anthraquinone dyes, triphenylmethane dyes and basic or acidic dyes, and natural direct dyes, alone or in a mixture with one another, for example 1,4-bis[(2-hydroxyethyl)amino]-2-nitrobenzene, 1-(2-hydroxyethyl)amino-2-nitro-4-[di(2-hydroxyethyl)amino]benzene, (HC Blue No. 2), 1-amino-3-methyl-4-[(2-hydroxyethyl)amino]-6-nitrobenzene, (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene, (HC Violet No. 2), 1-methylamino-4-[methyl-(2,3-dihydroxypropyl)amino]-2-nitrobenzene (HC Blue No. 6), 2-((4-amino-2-nitrophenyl)amino)-5-dimethylaminobenzoic acid (HC Blue No. 13), 1-(2-aminoethylamino)-4-[di(2-hydroxyethyl)amino]-2-nitrobenzene, 4-(di(2-hydroxyethyl)amino)-2-nitro-1-phenylaminobenzene, 1-amino-4-[(2-hydroxyethyl)amino]-2-nitrobenzene (HC Red No. 7), 2-amino-4,6-dinitrophenol, 1,4-diamino-2-nitrobenzene (CI76070), 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-((2-hydroxyethyl)methylamino)-1-(methylamino)-2-nitrobenzene, 1-amino-4-((2,3-dihydroxypropyl)amino)-5-methyl-2-nitrobenzene, 1-amino-4-(methylamino)-2-nitrobenzene, 4-amino-2-nitro-1-((prop-2-en-1-yl)amino)benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene, (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]-benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 6-amino-3-((2-hydroxyethyl)-amino)-2-nitropyridine, 3-amino-6-((2-hydroxyethyl)amino)-2-nitropyridine, 3-amino-6-(ethylamino)-2-nitropyridine, 3-((2-hydroxyethyl)amino)-6-(methylamino)-2-nitropyridine, 3-amino-6-(methylamino)-2-nitropyridine, 6-(ethylamino)-3-((2-hydroxyethyl)amino)-2-nitropyridine, 1,2,3,4-tetrahydro-6-nitroquinoxaline, 7-amino-3,4-dihydro-6-nitro-2H-1,4-benzoxazine (HC Red No. 14), 1,2-diamino-4-nitrobenzene (CI76020), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene, (HC Yellow No. 4), 1-[(2-hydroxyethyl)amino]-2-nitrobenzene (HC Yellow No. 2), 2-(di(2-hydroxyethyl)amino)-5-nitrophenol, 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride, (HC Yellow No. 9), 1-[(2-ureidoethyl)amino]-4-nitrobenzene, 4-[(2,3-dihydroxypropyl)amino]-3-nitro-1-trifluoromethylbenzene, (HC Yellow No. 6), 1-chloro-2,4-bis[(2-hydroxyethyl)amino]-5-nitrobenzene (HC Yellow No. 10), 1-amino-4-((2-aminoethyl)amino)-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene, (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 3-((2-hydroxyethyl)amino)-4-methyl-1-nitrobenzene, 4-chloro-3-((2-hydroxyethyl)amino)-1-nitrobenzene, 2,4-dinitro-1-hydroxynaphthalene, 1,4-di[(2,3-dihydroxypropyl)amino]-9,10-anthraquinone, 1,4-di[(2-hydroxyethyl)amino]-9,10-anthraquinone (CI61545, Disperse Blue 23), 1-[(2-hydroxyethyl)amino]-4-methylamino-9,10-anthraquinone (CI61505, Disperse Blue No. 3), 2-[(2-aminoethyl)amino]-9,10-anthraquinone (HC Orange No. 5), 1-amino-4-hydroxy-9,10-anthraquinone (CI60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-dioxo-3,5,6,8-tetrahydroxy-2-anthracenecarboxylic acid (CI75470, Natural Red 4), 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI62015, Disperse Red No. 11, Solvent Violet No. 26), 1,4-dihydroxy-5,8-bis[(2-hydroxyethyl)amino]-9,10-anthraquinone (CI62500, Disperse Blue No. 7, Solvent Blue No. 69), 1,4-diamino-9,10-anthraquinone (CI61100, Disperse Violet No. 1), 1-amino-4-(methylamino)-9,10-anthraquinone (CI61105, Disperse Violet No. 4, Solvent Violet No. 12), 2-hydroxy-3-methoxy-1,4-naphthoquinone, 2,5-dihydroxy-1,4-naphthoquinone, 2-hydroxy-3-methyl-1,4-naphthoquinone, N-(6-((3-chloro-4-(methylamino)phenyl)imino)-4-methyl-3-oxo-1,4-cyclohexadien-1-yl)urea (HC Red No. 9), 2-((4-(di(2-hydroxyethyl)amino)phenyl)amino)-5-((2-hydroxyethyl)amino)-2,5-cyclohexadiene-1,4-dione (HC Green No. 1), 5-hydroxy-1,4-naphthoquinone (CI75500, Natural Brown No. 7), 2-hydroxy-1,4-naphthoquinone (CI75480, Natural Orange No. 6), 1,2-dihydro-2-(1,3-dihydro-3-oxo-2H-indol-2-ylidene)-3H-indol-3-one (CI73000), 1,3-bis(dicyanomethylene)indane, 9-(dimethylamino)benzo[a]phenoxazin-7-ium chloride (CI51175; Basic Blue No. 6), di[4-(diethylamino)phenyl][4-(ethylamino)naphthyl]-carbenium chloride (CI42595; Basic Blue No. 7), di(4-(dimethylamino)phenyl)(4-(methylphenylamino)naphthalen-1-yl)carbenium chloride (CI42563; Basic Blue No. 8), 3,7-di(dimethylamino)phenothiazin-5-ium chloride (CI52015; Basic Blue No. 9), di[4-(dimethylamino)phenyl][4-(phenylamino)naphthyl]carbenium chloride (CI44045; Basic Blue No. 26), 2-[(4-(ethyl(2-hydroxyethyl)amino)-phenyl)azo]-6-ethoxy-3-methylbenzothiazolium methylsulfate (CI11154; Basic Blue No. 41), Basic Blue No. 77, 8-amino-2-bromo-5-hydroxy-4-imino-6-[(3-(trimethylammonio)phenyl)amino]-1(4H)-naphthalenone chloride (CI56059; Basic Blue No. 99), bis[4-(dimethylamino)phenyl][4-(methylamino)phenyl]carbenium chloride (CI42535; Basic Violet No. 1), tri(4-amino-3-methylphenyl)carbenium chloride (CI42520; Basic Violet No. 2), tris[4-(dimethylamino)phenyl]carbenium chloride (CI42555; Basic Violet No. 3), 2-[3,6-(diethylamino)dibenzopyranium-9-yl]benzoyl chloride (CI45170; Basic Violet No. 10), di(4-aminophenyl)(4-amino-3-methylphenyl)carbenium chloride (CI42510; Basic Violet No. 14), 1,3-bis[(2,4-diamino-5-methylphenyl)azo]-3-methylbenzene (CI21010; Basic Brown No. 4), 1-[(4-aminophenyl)azo]-7-(trimethylammonio)-2-naphthol chloride (CI12250; Basic Brown No. 16), 3-[(4-amino-2,5-dimethoxyphenyl)azo]-N,N,N-trimethylbenzenaminium chloride (CI112605, Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (CI12251; Basic Brown No. 17), 2-((4-aminophenyl)azo)-1,3-dimethyl-11H-imidazol-3-ium chloride (Basic Orange No. 31), 3,7-diamino-2,8-dimethyl-5-phenylphenazinium chloride (CI50240; Basic Red No. 2),1,4-dimethyl-5-[(4-(dimethylamino)phenyl)azo]-1,2,4-triazolium chloride (CI11055; Basic Red No. 22), 1,3-dimethyl-2-((4-dimethylamino)phenyl)-azo-1H-imidazol-3-ium chloride (Basic Red No. 51), 2-hydroxy-1-[(2-methoxyphenyl)azo]-7-(trimethylammonio)naphthalene chloride (CI12245; Basic Red No. 76), 2-[2-((2,4-dimethoxyphenyl)amino)ethenyl]-1,3,3-trimethyl-3H-indol-1-ium chloride (CI48055; Basic Yellow No. 11), 3-methyl-1-phenyl-4-[(3-(trimethylammonio)phenyl)azo]pyrazol-5-one chloride (CI12719; Basic Yellow No. 57), di[4-(dimethylamino)phenyl]-iminomethane hydrochloride (CI41000; Basic Yellow No. 2), 1-methyl-4-((methylphenylhydrazono)methyl)pyridinium methylsulfate (Basic Yellow No. 87), bis[4-(diethylamino)phenyl]phenylcarbenium hydrogensulfate (1:1) (CI42040; Basic Green No. 1), di(4-(dimethylamino)phenyl)-phenylmethanol (CI42000; Basic Green No. 4), 1-(2-morpholinium-propylamino)-4-hydroxy-9,10-anthraquinone methylsulfate, 1-[(3-(dimethylpropylaminium)propyl)amino]-4-(methylamino)-9,10-anthraquinone chloride, 1-[di(2-hydroxyethyl)amino]-3-methyl-4-[(4-nitrophenyl)azo]benzene (CI11210, Disperse Red No. 17), 1-[di(2-hydroxyethyl)amino]-4-[(4-nitrophenyl)azo]benzene (Disperse Black No. 9), 4-[(4-aminophenyl)azo]-1-[di(2-hydroxyethyl)amino]-3-methylbenzene, (HC Yellow No. 7), 2,6-diamino-3-[(pyridin-3-yl)azo]pyridine, 2-((4-(acetylamino)phenyl)azo)-4-methylphenol (CI11855; Disperse Yellow No. 3), 2-((4-(ethyl(2-hydroxyethyl)amino)-2-methylphenyl)azo)-5-nitro-1,3-thiazole (CI111935; Disperse Blue No. 106), 6-hydroxy-5-[(4-sulfophenyl)azo]-2-naphthalenesulfonic acid disodium salt (CI15985; Food Yellow No. 3; FD&C Yellow No. 6), 2,4-dinitro-1-naphthol-7-sulfonic acid disodium salt (CI10316; Acid Yellow No. 1; Food Yellow No. 1), 2-(indane-1,3-dion-2-yl)quinoline-x,x-sulfonic acid (mixture of mono- and disulfonic acid) (CI47005; D&C Yellow No. 10; Food Yellow No. 13, Acid Yellow No. 3), 5-hydroxy-1-(4-sulfophenyl)-4-[(4-sulfophenyl)azo]pyrazole-3-carboxylic acid trisodium salt (CI19140; Food Yellow No. 4; Acid Yellow No. 23), 9-(2-carboxyphenyl)-6-hydroxy-3H-xanthen-3-one (CI45350; Acid Yellow No. 73; D&C Yellow No. 8), 4-((4-amino-3-sulfophenyl)azo)benzenesulfonic acid disodium salt (CI13015, Acid Yellow No. 9), 5-[(2,4-dinitrophenyl)amino]-2-phenylaminobenzenesulfonic acid sodium salt (CI10385; Acid Orange No. 3), 4-[(2,4-dihydroxyphenyl)azo]benzenesulfonic acid monosodium salt (CI14270; Acid Orange No. 6), 4-[(2-hydroxynaphth-1-yl)azo]benzenesulfonic acid sodium salt (CI15510; Acid Orange No. 7), 4-((2-hydroxynaphthalen-1-yl)azo)-3-methylbenzenesulfonic acid sodium salt (CI15575; Acid Orange No. 8), 4-[(2,4-dihydroxy-3-[(2,4-dimethylphenyl)azo]phenyl)azo]-benzenesulfonic acid sodium salt (CI20170; Acid Orange No. 24), 3',6'-dihydroxy-4',5'-diiodospiro(isobenzofuran-1(3H)-9'-(9H)xanthen)-3-one (CI45425, D&C Orange No. 10), 4-hydroxy-3-[(4-sulfonaphth-1-yl)azo]-1-naphthalenesulfonic acid disodium salt (CI14720; Acid Red No. 14), 4-hydroxy-3-[(2-methoxyphenyl)azo]-1-naphthalenesulfonic acid monosodium salt (CI14710; Acid Red No. 4), 6-hydroxy-5-[(4-sulfonaphth-1-yl)azo]-2,4-naphthalenedisulfonic acid trisodium salt (CI16255; Ponceau 4R; Acid Red No. 18), 3-hydroxy-4-[(4-sulfonaphth-1-yl)azo]-2,7-naphthalenedisulfonic acid trisodium salt (CI16185; Acid Red No. 27), 8-amino-1-hydroxy-2-(phenylazo)-3,6-naphthalenedisulfonic acid disodium salt (CI17200; Acid Red No. 33), 5-(acetylamino)-4-hydroxy-3-[(2-methylphenyl)azo]-2,7-naphthalenedisulfonic acid disodium salt (CI18065; Acid Red No. 35), 2-(3-hydroxy-2,4,5,7-tetraiododibenzopyran-6-on-9-yl)benzoic acid disodium salt (CI45430; Acid Red No. 51). N-[6-(diethylamino)-9-(2,4-disulfophenyl)-3H-xanthen-3-ylidene]-N-ethylethaneammonium hydroxide, internal salt, sodium salt (CI45100; Acid Red No. 52), 8-[(4-(phenylazo)phenyl)azo]-7-naphthol-1,3-disulfonic acid disodium salt (CI27290; Acid Red No. 73), 2',4',5',7'-tetrabromo-3',6'-dihydroxyspiro[isobenzofuran-1(3H),9'-[9H]xanthen]-3-one disodium salt (CI45380; Acid Red No. 87), 2',4',5',7'-tetrabromo-4,5,6,7-tetrachloro-3',6'-dihydroxyspiro[isobenzofuran-1(3H), 9'-[9H]xanthen]-3-one disodium salt (CI45410; Acid Red No. 92), 3',6'-dihydroxy-4',5'-diiodospiro[isobenzofuran-1(3H),9'-(9H)-xanthen]-3-one disodium salt (CI45425; Acid Red No. 95), 2-hydroxy-3-((2-hydroxynaphth-1-yl)azo)-5-nitrobenzenesulfonic acid monosodium salt (CI15685; Acid Red No. 184) (2-sulfophenyl)di[4-(ethyl((4-sulfophenyl)methyl)amino)phenyl]carbenium disodium salt, betaine (CI42090; Acid Blue No. 9; FD&C Blue No. 1), 3-hydroxy-4-((4-methyl-2-sulfophenyl)azo)-2-naphthalenecarboxylic acid disodium salt (CI15850; D&C Red No. 6), 6-hydroxy-5-((2-methoxy-5-methyl-4-sulfophenyl)azo)-2-naphthalenesulfonic acid disodium salt (CI16035; FD&C Red 40), 1,4-bis[(2-sulfo-4-methylphenyl)amino]-9,10-anthraquinone disodium salt (CI61570; Acid Green No. 25), bis[4-(dimethylamino)phenyl](3,7-disulfo-2-hydroxynaphth-1-yl)carbenium internal salt, monosodium salt (CI44090; Food Green No. 4; Acid Green No. 50), bis[4-(diethylamino)phenyl](2,4-disulfophenyl)carbenium internal salt, sodium salt (2:1) (CI42045; Food Blue No. 3; Acid Blue No. 1), bis[4-(diethylamino)phenyl](5-hydroxy-2,4-disulfophenyl)carbenium internal salt, calcium salt (2:1) (CI42051; Acid Blue No. 3), 1-amino-4-(cyclohexylamino)-9,10-anthraquinone-2-sulfonic acid sodium salt (CI62045; Acid Blue No. 62), 3,3-bis(3,5-dibromo-4-hydroxyphenyl)-4,5,6,7-tetrabromo-2,1(3h)-benzoxathiole 1,1-dioxide, 1-amino-4-(phenylamino)-9,10-anthraquinone-2-sulfonic acid (CI62055; Acid Blue No. 25), 2-(1,3-dihydro-3-oxo-5-sulfo-2H-indol-2-ylidene)-2,3-dihydro-3-oxo-1H-indole-5-sulfonic acid disodium salt (CI73015; Acid Blue No. 74), 9-(2-carboxyphenyl)-3-[(2-methylphenyl)amino]-6-[(2-methyl-4-sulfophenyl)amino]-xanthylium internal salt, monosodium salt (CI45190; Acid Violet No. 9), 1-hydroxy-4-[(4-methyl-2-sulfophenyl)amino]-9,10-anthraquinone sodium salt (CI60730; D&C Violet No. 2; Acid Violet No. 43), bis[3-nitro-4-[(4-phenylamino)-3-sulfophenylamino]phenyl]-sulfone (CI10410; Acid Brown No. 13), 5-amino-4-hydroxy-6-[(4-nitrophenyl)azo]-3-(phenylazo)-2,7-naphthalenedisulfonic acid disodium salt (CI20470; Acid Black No. 1), 3-hydroxy-4-[(2-hydroxynaphth-1-yl)azo]-7-nitro-1-naphthalenesulfonic acid-chromium complex (3:2) (CI15711; Acid Black No. 52), 3-[(2,4-dimethyl-5-sulfophenyl)azo]-4-hydroxy-1-naphthalenesulfonic acid disodium salt (CI14700; Food Red No. 1; Ponceau SX; FD&C Red No. 4), 4-(acetylamino)-5-hydroxy-6-[(7-sulfo-4-[(4-sulfophenyl)azo]-naphth-1-yl)azo]-1,7-naphthalenedisulfonic acid tetrasodium salt (CI28440; Food Black No. 1) and 3-hydroxy-4-(3-methyl-5-oxo-1-phenyl-4,5-dihydro-1H-pyrazol-4-ylazo)naphthalene-1-sulfonic acid sodium salt, chromium complex (Acid Red No. 195).

The colorant (b) according to the invention, which comprises an oxidizing agent, preferably hydrogen peroxide, may, in addition to the dyes of the general formula (I), also comprise further oxidation-stable direct dyes, such as, for example, 3-(2',6'-diaminopyridyl-3'-azo)pyridine (=2,6-diamino-3-((pyridin-3-yl)azo)pyridine), N,N-di(2-hydroxyethyl)-3-methyl-4-((4-nitrophenyl)azo)aniline (Disperse Red 17, CI11210), 3-diethylamino-7-(4-dimethylaminophenylazo)-5-phenylphenazinium chloride (CI11050), 4-(2-thiazolylazo)resorcinol, 4-((4-phenylamino)azo)benzosulfonic acid sodium salt (Orange IV), 1-((3-aminopropyl)amino)-9,10-anthracenedione (HC Red No. 8), 3',3",4,5,5',5",6,7-octabromophenol sulfonephthalein (tetrabromophenol Blue), 1-((4-amino-3,5-dimethylphenyl)(2,6-dichlorophenyl)methylene)-3,5-dimethyl-4-imino-2,5-cyclohexadiene-phosphoric acid (1:1) (Basic Blue 77), 3',3",5',5"-tetrabromo-m-cresol sulfonephthalein, 2,4-dinitro-1-naphthol-7-sulfonic acid disodium salt (Acid Yellow 1, CI 10316), 4-[2'-hydroxy-1'-naphthyl)azo]benzosulfonic acid sodium salt (Acid Orange 7, CI15510), 3',6'-dihydroxy-2',4',5',7'-tetraiodospiro[isobenzofuran-1(3H), 9-(9H)xanthen]-3-one disodium salt (Acid Red 51, CI45430), 6-hydroxy-5-((2-methoxy-5-methyl-4-sulfophenyl)azo)-2-naphthalenesulfonic acid disodium salt (FD&C Red 40, CI16035), 2,4-dinitro-1-naphthol sodium salt (Acid Yellow 24; CI10315), 2',4',5',7'-tetrabromo-4,5,6,7-tetrachloro-3',6'-dihydroxyspiro(isobenzofuran-1(3H), 9'-[9H]xanthen)-3-one disodium salt (Acid Red 92, CI45410), 4-(2-hydroxy-1-naphthylazo)-3-methylbenzenesulfonic acid sodium salt (Acid Orange 8, CI15575), 2-amino-1,4-naphthalenedione, dithizone (1,5-diphenylthiocarbazone), N-((2-hydroxyethyl)-2-nitro-4-trifluoromethyl) aniline (HC Yellow 13), N-(2-hydroxyethyl)-4-nitroaniline and 4-chloro-N-(2,3-dihydroxypropyl)-2-nitroaniline, 1-methyl-4-((methylphenylhydrazono)methyl)pyridinium methylsulfate (Basic Yellow No. 87), 3-((4,5-dihydro-3-methyl-5-oxo-1-phenyl-1H-pyrazol-4-yl)azo)-N,N,N-trimethylbenzenaminium chloride, 3-[(3-methyl-5-hydroxy-1-phenyl-1H-pyrazol-4-yl)azo]-trimethylammoniobenzene chloride (Basic Yellow No. 57), 2-((4-aminophenyl)azo)-1,3-dimethyl-1H-imidazol-3-ium chloride (Basic Orange No. 31), 1,4-dimethyl-5-[(4-(dimethylamino)phenyl)azo]-1,2,4-triazolium chloride (Basic Red No. 22, CI11055), 2-((4-(dimethylamino)-phenyl)azo)-1,3-dimethyl-1H-imidazolium chloride (Basic Red No. 51), 1,4-dimethyl-5-[[4-[methyl (phenylmethyl)amino]-phenyl]azo]-1,2,4-triazolium bromide (Basic Red No. 46), N,N,N-trimethyl-3-[(4-(methylamino)-9,10-dioxo-9,10-dihydro-1-anthracenyl]amino 1-1-propanaminium methylsulfate, N,N-dimethyl-3-{[4-(methylamino)-9,10-dioxo-9,10-dihydro-1-anthracenyl]amino}-N-propyl-1-propanaminium chloride and N,N- dimethyl-3-{[4-(methylamino)-9,10-dioxo-9,10-dihydro-1-anthracenyl]amino}-N-propyl-1-propanaminium bromide.

The total content of additional dyes in the colorant according to the invention is from 0.01% to 15% by weight, in particular from 0.1% to 12% by weight.

The oxidation colorant (c) according to the invention, which is mixed prior to application with an oxidizing agent (in particular hydrogen peroxide or its addition compounds) or is oxidized by atmospheric oxygen, comprises in addition to the dyes of the general formula (I), oxidation dye precursors and if necessary one or more of the abovementioned additional direct dyes provided these are stable to the oxidizing agent used.

Suitable oxidation dye precursors are, for example, the following developer substances, coupler substances and self-coupling compounds:

(i) Developer substances: 1,4-diaminobenzene (p-phenylenediamine), 1,4-diamino-2-methylbenzene (p-tolylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-(2-(acetylamino)ethoxy)-1,4-diaminobenzene, 4-phenylaminoaniline, 4-dimethylaminoaniline, 4-diethylaminoaniline, 4-dipropylaminoaniline, 4-[ethyl(2-hydroxyethyl)-amino]aniline, 4-[di(2-hydroxyethyl)amino]aniline, 4-[di(2-hydroxyethyl)-amino]-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(2-hydroxyethyl)benzene, 1,4-diamino-2-(1-methylethyl)-benzene, 1,3-bis[(4-aminophenyl)(2-hydroxyethyl)amino]-2-propanol, 1,4-bis[(4-aminophenyl)amino]butane, 1,8-bis(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxyethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol, alone or in a mixture with one another.

(ii) Coupler substances: N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]-aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)-amino]aniline, 1,3-di(2,4-diaminophenoxy)propane, di(2,4-diamino-phenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)-amino]acetamide, 5-[(2-hydroxyethyl)amino]-4-methoxy-2-methylphenol, 5-[(2-hydroxyethyl)-amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)-amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxy-naphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole,2,3-indolenedione, alone or in a mixture with one another.

(iii) Self-coupling compounds: 2-amino-5-methylphenol, 2-amino-6-methylphenol.

The total amount of the oxidation dye precursors present in the colorant (c) according to the invention is from 0.01% to 12% by weight, in particular from 0.2% to 6% by weight.

To increase the color intensity, the carriers customary in cosmetic systems can be added if required. Suitable compounds are described, for example, in German Application No. DE 196 18 595 A1, to which hereby is explicitly referred. Particularly suitable carriers are, for example, benzyl alcohol, vanillin and isovanillin.

For coloring, the dyes described above are applied in a suitable color carrier mass.

The colorant (a), (b), or (c) according to the invention can also comprise all additives customary and known for such preparations, for example, perfume oils, complexing agents, waxes, preservatives, thickeners, antioxidants, alginates, guar gum, haircare substances, such as, for example, cationic polymers or lanolin derivatives, or anionic, nonionic, amphoteric or cationic surface-active substances. Preference is given to using amphoteric or nonionic surface-active substances, for example, betaine surfactants, propionates and glycinates, such as, for example, cocoamphoglycinates or cocoamphodiglycinates, ethoxylated surfactants with 1 ethylene oxide unit to 1000 ethylene oxide units, preferably with 1 ethylene oxide unit to 300 ethylene oxide units, such as, for example, glyceride alkoxylates, for example, castor oil ethoxylated with 25 ethylene oxide units, polyglycolamides, ethoxylated alcohols and ethoxylated fatty alcohols (fatty alcohol alkoxylates) and ethoxylated fatty acid sugar esters, in particular ethoxylated sorbitan fatty acid esters. The above-mentioned constituents are used in the amounts customary for such purposes, for example, the surface-active substances in a concentration of from 0.1% to 30% by weight, and the care substances in an amount of from 0.1% to 5% by weight.

The colorant (a), (b), or (c) according to the invention can, particularly if it is a hair colorant, be present in the form of a powder or granules which is/are dissolved prior to application in an aqueous or aqueous-alcoholic preparation, or else in the form of an aqueous or aqueous-alcoholic solution, a cream, a gel, an emulsion or an aerosol foam, where the colorant can be formulated either in the form of a single-component preparation or else in the form of a multicomponent preparation, for example, in the form of a two-component preparation in which the particular dye derivative of the general formula (I) is packaged separately from the other constituents and the ready-to-use colorant is only prepared directly prior to application by mixing the two components.

The colorant (a), (b), or (c) according to the invention generally has a pH of 2 to 11, preferably 5 to 10. Both organic and inorganic acids or bases are suitable for adjusting the pH according to the invention. Examples of suitable acids are, in particular, the following acids: α-hydroxycarboxylic acids, such as, for example, glycolic acid, lactic acid, tartaric acid, citric acid or malic acid, ascorbic acid, gluconic acid lactone, acetic acid, hydrochloric acid or phosphoric acid, and mixtures of these acids. Examples of suitable bases are, in particular, sodium carbonate, sodium hydrogencarbonate, organic amines, for example, monoethanolamine, triethanolamine, 2-amino-2-methyl-1-propanol or tris(hydroxymethyl)aminomethane, ammonia, potassium hydroxide and sodium hydroxide, and mixtures thereof.

Depending on the intended use, the colorant according to the invention can be used with one or more synthetic oxidizing agents (lightening; oxidation colorants) or without a synthetic oxidizing agent (nonoxidative colorants; oxidation by air).

Oxidizing Agent

The compositions according to the present invention may comprise at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolourisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates, etc. Alkyl and aryl peroxides, and or peroxidases may also be used. Mixtures of two or more such oxidizing agents can also be used if desired. The oxidizing agents may be provided in aqueous solution or as a powder which is dissolved prior to use. Preferred for use in the compositions according to the present invention are hydrogen peroxide, percarbonate, persulphates, and combinations thereof.

According to the present invention the compositions comprise from 0.1% to 15% by weight, preferably from 1% to 10% by weight, and most preferably from 2% to 7% by weight of an oxidizing agent.

Another preferred oxidizing agent for use herein is a source of peroxymonocarbonate ions. Preferably such a source is formed in situ from a source of hydrogen peroxide and a hydrogen carbonate ion source. Such an oxidizing agent has been found to be particularly effective at a pH of up to and including 9.5, preferably 7.5 to 9.5 more preferably pH 9. Moreover, this system is also particularly effective in combination with a source of ammonia or ammonium ions. It has been found that this oxidizing agent can deliver improvements to the desired hair color results particularly with regard to the delivery of high lift, while considerably reducing the odor, skin and scalp irritation, and damage to the hair fibers.

Accordingly, any source of these ions may be utilized. Suitable sources for use herein include sodium, potassium, guanidine, arginine, lithium, calcium, magnesium, barium, ammonium salts of carbonate, carbamate and hydrocarbonate ions, and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate, and mixtures thereof. Percarbonate salts may also be utilized to provide both the source of carbonate ions and oxidizing agent. Preferred sources of carbonate ions, carbamate and hydrocarbonate ions are sodium hydrogen carbonate, potassium hydrogen carbonate, ammonium carbamate, and mixtures thereof.

According to the present invention the compositions comprise from 0.1% to 15% by weight, preferably from 1% to 10% by weight, and most preferably from 1% to 8% by weight of a hydrogencarbonate ion and from 0.1% to 0% by weight, preferably from 1% to 7% by weight, and most preferably from 2% to 5% by weight of a source of hydrogen peroxide.

Alkalizing Agent

According to the present invention the composition may further optionally comprise at least one source of alkalizing agent, preferably a source of ammonium ions and or ammonia. Any agent known in the art may be used such as alkanolamides, for example, monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, and guanidium salts. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia, and mixtures thereof. Particularly preferred are ammonium carbonate, ammonium carbamate, ammonium hydrogen carbonate, ammonia, and mixtures thereof. The compositions of the present invention may comprise from 0.1% to 10% by weight, preferably from 0.5% to 5%, most preferably from 1% to 3% of an alkalizing agent, preferably ammonium ions.

Radical Scavenger

According to the present invention the compositions may further comprise a source of radical scavenger. As used herein the term radical scavenger refers to a species that can react with a reactive radical, preferably carbonate radicals, to convert the reactive radical by a series of fast reactions to a less reactive species.

Suitable radical scavengers for use herein include compounds according to the general formula (RS I): $R^1$—Y—C(H)($R^3$)—$R^4$—(C(H)($R^5$)—Y—$R^6$)$_n$ wherein Y is $NR^2$, O, or S, preferably $NR^2$, n is 0 to 2, and wherein $R^4$ is monovalent or divalent and is selected from: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or perfluoro alkyl systems; the systems of (i), (ii), and (iii) comprising from 1 carbon atom to 12 carbon atoms and 0 heteroatoms to 5 heteroatoms selected from O, S, N, P, and Si; and wherein $R^4$ can be connected to $R^3$ or $R^5$ to create a 5, 6, or 7 membered ring; and wherein $R^1$, $R^2$, $R^3$, $R^5$, and $R^6$ are monovalent and are selected independently from: (i), (ii), and (iii) described herein above, or H.

Preferably, $R^4$ is selected from: (i) substituted or unsubstituted, straight or branched, alkyl, heteroalkyl, aliphatic, heteroaliphatic, or heteroolefinic systems, (ii) substituted or unsubstituted, mono- or poly-cyclic aliphatic, aryl, or heterocyclic systems; or (iii) substituted or unsubstituted, mono-, poly-, or per-fluoro alkyl systems; more preferably $R^4$ is selected from (i) substituted or unsubstituted, straight or branched, alkyl, heteroalkyl, aliphatic, or heteroaliphatic systems; (ii) substituted or unsubstituted, aryl, or heterocyclic systems; or (iii) substituted or unsubstituted, mono-, poly-, or per-fluoro alkyl systems; more preferably substituted or unsubstituted, straight or branched, alkyl, or heteroalkyl systems.

Preferably, the $R^4$ systems of (i), (ii), and (iii), described herein above, comprise from 1 carbon atom to 8 carbon atoms, preferably from 1 carbon atom to 6 carbon atoms, more preferably from 1 carbon atom to 4 carbon atoms and from 0 heteroatoms to 3 heteroatoms; preferably from 0 heteroatoms to 2 heteroatoms; most preferably from 0 heteroatoms to 1 heteroatom. Where the systems contain heteroatoms, preferably they contain 1 heteroatom. Preferred heteroatoms include O, S, and N; more preferred are O, and N; and most preferred is O.

Preferably, $R^1$, $R^2$, $R^3$, $R^5$, and $R^6$ are selected independently from any of the systems defined for $R^4$ above, and H.

In alternative embodiments, any of $R^1$, $R^2$, $R^3$, $R^4$, $R^5$, and $R^6$ groups are substituted. Preferably, the substituent(s) is selected from: (i) the group of C-linked monovalent substituents consisting of: substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; or substituted or unsubstituted, mono-, poly-, or per-fluoro alkyl systems; said systems comprising from 1 carbon atom to 10 carbon atoms and 0 heteroatoms to 5 heteroatoms selected from O, S, N, P, and Si; (ii) the group of S-linked monovalent substituents consisting of $SA^1$, SCN, $SO_2A^1$, $SO_3A^1$, $SSA^1$, $SOA^1$, $SO_2NA^1A^2$, $SNA^1A^2$, and $SONA^1A^2$; (iii) the group of O-linked monovalent substituents consisting of $OA^1$, OCN and $ONA^1A^2$; (iv) the group of N-linked monovalent substituents consisting of $NA^1A^2$, $(NA^1A^2A^3)^+$, NC, $NA^1OA^2$, $NA^1SA^2$, NCO, NCS, $NO_2$, N=$NA^1$, N=$NOA^1$, $NA^1CN$, $NA^1NA^2A^3$; (v) the group of monovalent substituents consisting of $COOA^1$, $CON_3$, $CONA^1_2$, $CONA^1COA^2$, C(=$NA^1$)$NA^1A^2$, CHO, CHS, CN, NC, and X; and (vi) the group consisting fluoroalkyl monovalent substituents consisting of mono-, poly-, or per-fluoro alkyl systems comprising from 1 carbon atom to 12 carbon atoms and 0 heteroatoms to 4 heteroatoms.

For the groups (ii) to (v), described above, $A^1$, $A^2$, and $A^3$ are monovalent and are independently selected from: (1) H; (2) substituted or unsubstituted, straight or branched, alkyl, mono- or poly-unsaturated alkyl, heteroalkyl, aliphatic, heteroaliphatic, or heteroolefinic systems; (3) substituted or unsubstituted, mono- or poly-cyclic aliphatic, aryl, or heterocyclic systems; or (4) substituted or unsubstituted, mono-, poly-, or per-fluoro alkyl systems; said systems of (2), (3), and (4) comprising from 1 carbon atom to 10 carbon atoms and 0 heteroatoms to 5 heteroatoms selected from O, S, N, P, and Si; and wherein X is a halogen selected from the group consisting of F, Cl, Br, and I.

Preferred substituents for use herein include those having a Hammett Sigma Para ($\sigma_p$) Value from −0.65 to +0.75, preferably from −0.4 to +0.5. Hammett Sigma Values are described in *Advanced Organic Chemistry—Reactions, Mechanisms and Structure* (Jerry March, 5$^{th}$ ed. (2001) at pages 368-375).

Alternative suitable radical scavengers for use herein are compounds according to the general formula (RS II):

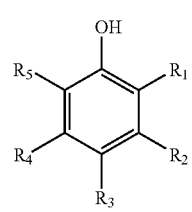

(RS II)

wherein $R_1$, $R_2$, $R_3$, $R_4$, and $R_5$ are each independently selected from H, $COO^-M^+$, Cl, Br, $SO_3^-M^+$, $NO_2$, $OCH_3$, OH or a $C^1$ to $C^{10}$ primary or secondary alkyl and M is either H or alkali metal. Preferably, the above-described radical scavengers have a pKa of more than 8.5 to ensure protonation of the hydroxy group.

Other suitable radical scavengers for use herein include those selected from group (RS III) benzylamine, imidazole, di-tert-butylhydroxytoluene, hydroquinone, guanine, pyrazine, piperidine, morpholine, methylmorpholine, 2-methoxyethylamine, and mixtures thereof.

Preferred radical scavengers according to the present invention are selected from the classes of alkanolamines, amino sugars, amino acids, esters of amino acids, and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof. Especially preferred compounds are glycine, sarcosine, lysine, serine, 2 methoxyethylamine, glucosamine, glutamic acid, morpholine, piperidine, ethylamine, 3 amino-1-propanol and mixtures thereof.

The radical scavengers according to the present invention preferably have a molecular weight of less than 500, preferably less than 300, more preferably less than 250 in order to facilitate penetration of the radical scavenger into the hair fiber. The compositions of the present invention preferably comprise from 0.1% to 10% by weight, preferably from 1% to 7% by weight of radical scavenger. The radical scavenger is also preferably selected such that it is not an identical species as the alkalizing agent. According to one embodiment of the present invention the radical scavenger may be formed in situ in the hair dyeing compositions prior to application to the hair fibers.

If required, the agent for coloring keratin fibers prior to application is mixed with an oxidizing agent. Suitable oxidizing agents are primarily hydrogen peroxide or its addition compounds onto urea, melamine, sodium borate or sodium carbonate in the form of a 1% to 12% strength, preferably a 3% to 9% strength, aqueous solution. In the case of agents with simultaneous lightening or bleaching, depending on the dye of the formula (I) used it is additionally possible to add persulfates, e.g., ammonium persulfate, potassium persulfate, or sodium persulfate. The weight ratio between color carrier mass and oxidizing agent is here preferably 5:1 to 1:3, in particular 1:1 to 1:2. Larger amounts of oxidizing agent are used especially at higher concentrations of oxidative dye precursors in the colorant, or if greater bleaching of the keratin fibers (in particular of the hair) is intended at the same time.

The colorant according to the invention is generally used by applying an amount of the hair colorant sufficient for the hair coloring, 30 grams to 200 grams depending on hair length, to the hair, allowing the hair colorant to act at 15° C. to 50° C. for 1 minute to 60 minutes, preferably 5 minutes to 30 minutes, then rinsing the hair thoroughly with water, optionally washing with a shampoo and/or after-treating with a hair-conditioning composition, and finally drying.

In addition, if no oxidizing agents are added to the coloring mass, the above-described colorant can comprise natural or synthetic polymers or modified polymers of natural origin customary for cosmetic compositions, as a result of which setting of the hair is achieved at the same time as the coloring. Such compositions are generally referred to as tinting setting compositions or color setting compositions.

Of the synthetic polymers known for this purpose in cosmetics, mention may be made, for example, of polyvinylpyrrolidone, polyvinyl acetate, polyvinyl alcohol or polyacrylic compounds, such as polyacrylic acid or polymethacrylic acid, basic polymers of esters of polyacrylic acid, polymethylacrylic acid and amino alcohols, for example, salts or quaternization products thereof, polyacrylonitrile, polyvinyl acetates, and copolymers of such compounds, such as, for example, polyvinylpyrrolidone-vinyl acetate; while natural polymers or modified natural polymers which can be used are, for example, chitosan (deacetylated chitin) or chitosan derivatives.

The abovementioned polymers may be present in the colorant (a) according to the invention in the amounts customary for such agents, in particular in an amount of from 1% to 5% by weight. The pH of the tinting setting composition or color setting composition according to the invention is preferably 4 to 10.

The hair colorant with additional setting is used in a known and customary manner by wetting the hair with the setting composition, arranging (styling) the hair into the hairstyle and then drying.

The colorant with pendant cationic azodyes of the formula (I) permits, inter alia, a simple and gentle coloration of hair with varying degrees of damage (for example, recolorations of sections of hair which have already been oxidatively colored), the color carrier mass without oxidizing agent—neat or mixed with an acidic, neutral or basic aqueous diluent—being applied to the predamaged sections of hair (for example, the hair ends), while the color carrier mass mixed with the oxidizing agent is applied to the sections of hair with little or no predamage (for example, the new hair growth). The aqueous component used for dilution can comprise the abovementioned customary additives for solutions, creams, emulsions, or gels. This process allows colorations matched to the nature of the hair which are characterized by a hair-gentle evening out between roots and ends, which is not possible when using customary oxidative hair colorants since an oxidizing agent is always required to couple the dye precursors.

The colorant according to the invention permits a coloration of keratin fibers, in particular of human hair, with very strong color intensity and brilliance, a good eveness of color between damaged and undamaged hair (such as, for example, between hair ends and new hair growth), very good durability (washing fastness), very good mildness to the hair and variable application options with and without oxidizing agents.

The dyes of formula (I) can be prepared analogously to known preparation processes, such as, for example, in a one step procedure, via diazotation of 1,3-thiazol-2-amine, 1H-imidazol-2-amine, 1,2,4-thiadiazol-5-amine, 1,3,4-thiadiazol-2-amine, 4H-1,2,4-triazol-3-amine, or the like, and coupling with cationic aniline derivatives, or in a 2-step procedure via diazotation of 1,3-thiazol-2-amine, 1H-imidazol-2-amine, 1,2,4-thiadiazol-5-amine, 1,3,4-thiadiazol-2-amine, 4H-1,2,4-triazol-3-amine, or the like, and coupling with bromoalkyl-aniline derivatives, followed by quaternization with tertiary amines.

Some dyes of the formula (I) are known as textile dyes.

The examples below are intended to illustrate the subject-matter of the invention in more detail without limiting it thereto.

EXAMPLES

Example 1

1-Step Procedure

Example 1a

2-[{4-[(4,5-dimethyl-1,3-thiazol-2-yl)diazenyl]phenyl}(ethyl)-amino]-N,N,N-trimethylethanaminium Bromide (Standard Azocoupling Procedure)

11.5 g 2-amino-4,5-dimethyl-1,3-thiazol hydrochloride is dissolved in a mixture of 300 ml acetic acid and 10.2 g sulphuric acid while the temperature rises up to 30° C. The mixture is cooled to 15° C. followed by dropwise addition of 33.2 g 40% aqueous nitrosyl sulphuric acid and is stirred for 1.5 hours. In a separate beaker a solution of 20 g 2-[ethyl (phenyl)amino]-N,N,N-trimethylethanaminium bromide in a mixture of 80 ml acetic acid, 8.3 g hydrochloric acid and 120 g ice was prepared. The previously prepared diazonium salt solution was added slowly to this solution so that the temperature does not exceed 5° C. The solution is further stirred for 2 hours at room temperature. The pH value is adjusted to 4 by adding an appropriate amount of 30% aqueous sodium hydroxide. The resulted precipitate is filtered off, washed with water, and dried in vacuum at 40° C. After recrystallization in ethanol/water, 20.3 g of 2-[{4-[(4,5-dimethyl-1,3-thiazol-2-yl)diazenyl]phenyl}(ethyl)amino]-N,N,N-trimethylethanaminium bromide is obtained as red crystals.

$^1$H NMR (300 MHz, DMSO): δ=7.78 (d, J=9.3, 2H, H(3) and H(5)-phenyl); 6.94 (d, J=9.3, 2H, H(2) and H(6)-phenyl); 3.91 (m, 2H, N$^+$CH2); 3.55 (m, 4H, 2×NCH2); 3.21 (s, 9H, 3×CH3); 2.38 (s, 3H, CH3); 2.32 (s, 3H, CH3); 1.19 (t, J=6.9, 3H, CH3).

FAB-MS: 346 [M$^+$] (100)

Example 1b

2-[{4-[(4,5-dimethyl-1,3-thiazol-2-yl)diazenyl]-3-methylphenyl}(ethyl)amino]-N,N,N-trimethylethanaminium Bromide Analogously to the procedure described in example 1a, by azocoupling of 2-amino-4,5-dimethyl-1,3-thiazol hydrochloride with 2-[ethyl(3-methylphenyl)amino]-N,N,N-trimethylethanaminium bromide to give 2-[{4-[(4,5-dimethyl-1,3-thiazol-2-yl)diazenyl]-3-methylphenyl}(ethyl)amino]-N,N,N-trimethylethanaminium bromide in 55% yield.

$^1$H NMR (300 MHz, DMSO): δ=7.70 (d, J=9.0, 1H, H(5)-phenyl); 6.77 (dd, J=9.0, J=2.7, 1H, H(6)-phenyl); 6.75 (d, J=2.7, 1H, H(2)-phenyl); 3.90 (m, 2H, N CH2); 3.52 (m, 4H, 2×NCH2); 3.21 (s, 9H, 3×CH3); 2.57 (s, 3H, CH3); 2.37 (s, 3H, CH3); 2.31 (s, 3H, CH3); 1.18 (t, J=6.9, 3H, CH3).

Example 1c

2-[{3-chloro-4-[(4,5-dimethyl-1,3-thiazol-2-yl)diazenyl]-phenyl}(ethyl)amino]-N,N,N-trimethylethanaminium Methyl Sulfate Analogously to the procedure described in example 1a, by azocoupling of 2-amino-4,5-dimethyl-1,3-thiazol hydrochloride with 2-[(3-chlorophenyl)-(ethyl)amino]-N,N,N-trimethylethanaminium methyl sulfate to give 2-[{3-chloro-4-[(4,5-dimethyl-1,3-thiazol-2-yl)diazenyl]phenyl}(ethyl)-amino]-N,N,N-trimethylethanaminium methyl sulfate in 44% yield.

$^1$H NMR (300 MHz, DMSO): δ=7.78 (d, J=9.3, 1H, H(5)-phenyl); 7.00 (d, J=2.4, 1H, H(2)-phenyl); 6.90 (dd, J=9.0, J=2.7, 1H, H(6)-phenyl); 3.92 (m, 2H, N$^+$CH2); 3.55 (m, 4H, 2×NCH2); 3.19 (s, 9H, 3×CH3); 2.39 (s, 3H, CH3); 2.33 (s, 3H, CH3); 1.18 (t, J=6.9, 3H, CH3).

Examples 2 to 4

Hair Colorant

| | |
|---|---|
| 0.33 g | Dye of the formula (I) according to table 1 |
| 5.0 g | Ethanol |
| 4.0 g | Decyl glucoside |
| 0.2 g | Ethylenediaminotetraacetic acid disodium salt |
| balance to 100.0 g | Water, demineralized |

If necessary, the coloring solution is adjusted to the pH values given in Table 1 by adding ammonia.

The hair coloring is carried out by applying an amount of the colorant sufficient for the hair coloring to the hair and distributing it evenly using a brush. After a contact time of 30 minutes at 40° C., the hair is rinsed with lukewarm water, washed with a shampoo, rinsed with lukewarm water, and then dried.

The coloring results are summarized in Table 1 below.

TABLE 1

| Ex. | Compound of the formula (I) (as in examples 1a-1c) | pH of the colorant | Color-shade after coloring | Color-measurement values after coloring |
|---|---|---|---|---|
| — | Color shade of the hair before the coloring treatment | — | — | L = 80.60<br>C = 12.10<br>h = 92.10 |
| 2 | 2-[{4-[(4,5-dimethyl-1,3-thiazol-2-yl)diazenyl]phenyl}(ethyl)-amino]-N,N,N-trimethylethanaminium bromide (1a) | 9.6 | red-orange | L = 40.93<br>C = 68.59<br>h = 37.3 |
| 3 | 2-[{4-[(4,5-dimethyl-1,3-thiazol-2-yl)diazenyl]-3-methylphenyl}-(ethyl)amino]-N,N,N-trimethyl-ethanaminium bromide (1b) | 9.5 | red | L = 38.13<br>C = 65.52<br>h = 34.8 |
| 4 | 2-[{3-chloro-4-[(4,5-dimethyl-1,3-thiazol-2-yl)diazenyl]-phenyl}(ethyl)amino]-N,N,N-trimethylethanaminium methyl sulfate (1c) | 9.4 | red-orange | L = 45.72<br>C = 70.63<br>h = 42.3 |

Examples 5 to 7

Hair Colorant with Oxidizing Agent

| | |
|---|---|
| 0.66 g | Dye of the formula (I) according to table 2 |
| 5.0 g | Ethanol |
| 4.0 g | Decyl glucoside |
| 0.2 g | Ethylenediaminotetraacetic acid disodium salt |
| balance to 100.0 g | Water, demineralized |

5 g of the above color carrier mass is mixed with 5 g of a 9% strength hydrogen peroxide solution. The pH is adjusted to the basic pH values given in Table 2, using 25% strength ammonia.

The resulting ready-to-use hair colorant is applied to the hair and distributed evenly using a brush. After a contact time of 30 minutes at 40° C., the hair is rinsed with lukewarm water, washed with a shampoo, rinsed again with lukewarm water, and then dried.

The coloring results are summarized in Table 2 below.

TABLE 2

| Ex. | Compound of the formula (I) (as in examples 1a-1c) | pH of the colorant | Color shade after coloring | Color measurement values after coloring |
|---|---|---|---|---|
| — | Color shade of the hair before the coloring treatment | — | — | L = 80.60<br>C = 12.10<br>h = 92.10 |
| 5 | 2-[{4-[(4,5-dimethyl-1,3-thiazol-2-yl)diazenyl]phenyl}(ethyl)-amino]-N,N,N-trimethylethanaminium bromide (1a) | 9.0 | red-orange | L = 44.96<br>C = 72.13<br>h = 40.1 |
| 6 | 2-[{4-[(4,5-dimethyl-1,3-thiazol-2-yl)diazenyl]-3-methylphenyl}-(ethyl)amino]-N,N,N-trimethyl-ethanaminium bromide (1b) | 9.2 | red | L = 41.08<br>C = 67.76<br>h = 36.00 |
| 7 | 2-[{3-chloro-4-[(4,5-dimethyl-1,3-thiazol-2-yl)diazenyl]-phenyl}(ethyl)amino]-N,N,N-trimethylethanaminium methyl sulfate (1c) | 9.4 | red-orange | L = 45.99<br>C = 72.11<br>h = 40.9 |

Example 8

Hair Colorant without Oxidizing Agent

| | |
|---|---|
| 0.33 g | Dye of the formula (I) according to table 3 |
| 5.0 g | Ethanol |
| 4.0 g | Decyl glucoside |
| 0.2 g | Ethylenediaminotetraacetic acid disodium salt |
| balance to 100.0 g | Water, demineralized |

The pH is adjusted to the given pH in Table 3 using 25% strength ammonia.

The resulting ready-to-use hair colorant is applied to natural hair (L=34.24, C=14.62, h=66.7) and distributed evenly using a brush. After a contact time of 30 minutes at 40° C., the hair is rinsed with lukewarm water, washed with a shampoo, rinsed again with lukewarm water, and then dried. The washing process is repeated five times. The colors do not change visually.

TABLE 3

| Ex. | Compound of the formula (I) | pH of the colorant | Color shade after coloring | Color shade after washing |
|---|---|---|---|---|
| 8 | 2-[{4-[(4,5-dimethyl-1,3-thiazol-2-yl)diazenyl]phenyl}-(ethyl)amino]-N,N,N-trimethylethanaminium bromide (1a) | 9.4 | mahogany<br>L = 27.03<br>C = 23.11<br>h = 42.7 | mahogany<br>L = 29.48<br>C = 23.11<br>h = 47.1 |

Example 9

Hair Colorant with Oxidizing Agent

| | |
|---|---|
| 0.66 g | Dye of the formula (I) according to table 4 |
| 5.0 g | Ethanol |
| 4.0 g | Decyl glucoside |
| 0.2 g | Ethylenediaminotetraacetic acid disodium salt |
| balance to 100.0 g | Water, demineralized |

5 g of the above color carrier mass is mixed with 5 g of a 9% strength hydrogen peroxide solution. The pH is adjusted to the given pH in Table 4 using 25% strength ammonia.

The resulting ready-to-use hair colorant is applied to natural hair (L=34.24, C=14.62, h=66.7) and distributed evenly using a brush. After a contact time of 30 minutes at 40° C., the hair is rinsed with lukewarm water, washed with a shampoo, rinsed again with lukewarm water, and then dried. The washing process is repeated five times. The colors do not change visually.

TABLE 4

| Ex. | Compound of the formula (I) | pH of the colorant | Color shade after coloring | Color shade after washing |
|---|---|---|---|---|
| 9 | 2-[{4-[(4,5-dimethyl-1,3-thiazol-2-yl)diazenyl]phenyl}-(ethyl)amino]-N,N,N-trimethyl-ethanaminium bromide (1a) | 9.4 | mahogany-orange<br>L = 30.16<br>C = 26.83<br>h = 46.2 | mahogany-orange<br>L = 32.60<br>C = 25.69<br>h = 51.0 |

Example 10

Hair Colorant with Cationic Surface-Active Substances

| | |
|---|---|
| 0.33 g | 2-[{4-[(4,5-dimethyl-1,3-thiazol-2-yl)diazenyl]phenyl}(ethyl)-amino]-N,N,N-trimethylethanaminium bromide (1a) |
| 5.00 g | Ethanol |
| 4.00 g | Cetyltrimethylammonium chloride, 25% in water |
| balance to 100.00 g | Water, demineralized |

The pH is adjusted to 9.8 using 25% strength ammonia.

The hair coloring is carried out by applying an amount of the colorant sufficient for the hair coloring to the hair (L=80.6; C=12.1 h=92.1) and distributing it evenly using a brush. After a contact time of 30 minutes at 40° C., the hair is rinsed with lukewarm water, washed with a shampoo, rinsed again with lukewarm water, and then dried.

This gives an intensely red-orange colored switch (L=46.30; C=72.01; h=42.2).

Example 11

Hair Colorant with Amphoteric Surface-Active Substances

| | |
|---|---|
| 0.33 g | 2-[{4-[(4,5-dimethyl-1,3-thiazol-2-yl)diazenyl]phenyl}(ethyl)-amino]-N,N,N-trimethylethanaminium bromide (1a) |
| 5.00 g | Ethanol |
| 7.50 g | Coconut fatty acid amidopropylbetaine |
| balance to 100.00 g | Water, demineralized |

The pH is adjusted to 9.4 using 25% strength ammonia.

The hair coloring is carried out by applying an amount of the colorant sufficient for the hair coloring to the hair (L=80.6; C=12.1; h=92.1) and distributing it evenly using a brush. After a contact time of 30 minutes at 40° C., the hair is rinsed with lukewarm water, washed with a shampoo, rinsed again with lukewarm water, and then dried.

This gives an intensely red-orange colored switch (L=45.30; C=71.68; h=40.3).

The L*C*h* color measurement values given in the preceding examples were measured using a calorimeter from Minolta, model Chromameter II. The L value is the lightness (i.e., the lower the L value, the greater the color intensity), while the C value is a measure of the colorfulness ("chroma") (i.e., the greater the C value, the more colorful the color). The h value is the color shade angle ("hue").

Unless stated otherwise, all of the percentages given in the present application are percentages by weight.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A keratin dyeing composition comprising:
   (a) a medium suitable for dyeing;
   (b) at least one azodye of general formula (I) to the keratin fibers:

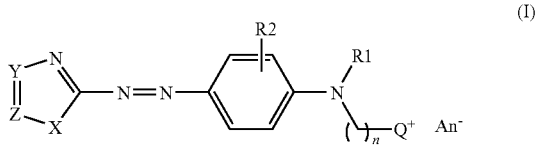

wherein
   X is selected from the group consisting of oxygen, sulfur, N—R3 and C—R4;
   Y is selected from the group consisting of C—R5, nitrogen, N—R6, sulfur and oxygen;
   Z is C—R7 or nitrogen;
   with the proviso that the heterocycle of the formula (I) comprises at least two and at most three heteroatoms, where the heterocycle has at most one sulfur atom or one oxygen atom;
   n is an integer from 1 to 6;
   R1 is selected from the group consisting of hydrogen, a saturated or unsaturated ($C_1$-$C_{12}$)-alkyl group, a ($C_1$-$C_{12}$)-alkyl group substituted by a halogen atom, a hydroxy-($C_2$-$C_{12}$)-alkyl group, an amino-($C_1$-$C_{12}$)-alkyl group, a substituted or unsubstituted phenyl group and a substituted or unsubstituted benzyl group;
   R2, R4, R5 and R7 may be identical or different and, independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a ($C_1$-$C_{12}$)-thioalkyl group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group, a substituted or unsubstituted naphthyl group and a substituted or unsubstituted heteroaryl group;
   or if Y and Z are C—R5 and C—R7, the radical groups R5 and R7, together with the remaining molecule, can form a heterocyclic or carbocyclic, saturated or unsaturated, substituted or unsubstituted ring system;
   or if X and Y are C—R4 and C—R5, the radical groups R4 and R5, together with the remaining molecule, can form a heterocyclic or carbocyclic, saturated or unsaturated, substituted or unsubstituted ring system;
   R3 and R6 may be identical or different and, independently of one another, are selected from the group consisting of a saturated or unsaturated ($C_1$-$C_{12}$)-alkyl group, a ($C_1$-$C_{12}$)-alkyl group substituted by a halogen atom (F, Cl, Br, I), a hydroxy-($C_2$-$C_{12}$)-alkyl group, an amino-($C_1$-$C_{12}$)-alkyl group, a substituted or unsubstituted phenyl group and a substituted or unsubstituted benzyl group;
   Q+ represents a quaternary monoalkylammonium, dialkylammonium or trialkylammonium group, where the alkylgroups may be identical or different and, independently of one another, are a saturated or unsaturated ($C_1$-$C_{12}$)-alkyl group;
   with the proviso that when Q+ represents a tri($C_1$-$C_4$) alkylammonium group, and X is sulfur and Y is nitrogen or a CH group, Z is not a C—R5 residue with R5 representing hydrogen, a halogen atom, a nitro group or an alkylgroup;
   or Q+ represents a quaternary monoarylammonium, diarylammonium or triarylammonium group, where the arylgroups may be identical or different and, independently of one another, are an unsubstituted or substituted phenylgroup;
   or Q+ represents a quaternary alkylarylammonium group, where the alkylgroups may be identical or different and, independently of one another, are a saturated or unsaturated ($C_1$-$C_{12}$)-alkyl group, and the arylgroups may be identical or different and, independently of one another, are an unsubstituted or substituted phenylgroup;
   the anion An- is an organic or inorganic acid anion and;
   (c) at least one additional direct dye which is selected from the group consisting of nitro dyes, azodyes, anthraquinone dyes, triphenylmethane dyes, basic dyes or acidic dyes.

2. A method of coloring keratin fibers, comprising applying at least one azodye of general formula (I) to the keratin fibers:

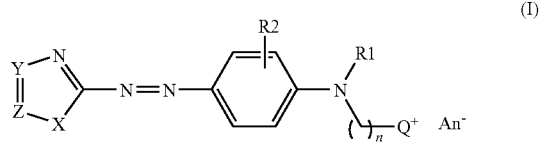

wherein
   X is selected from the group consisting of oxygen, sulfur, N—R3 and C—R4;
   Y is selected from the group consisting of C—R5, nitrogen, N—R6, sulfur and oxygen,
   Z is C—R7 or nitrogen;
   with the proviso that the heterocycle of the formula (I) comprises at least two and at most three heteroatoms, where the heterocycle has at most one sulfur atom or one oxygen atom;
   n is an integer from 1 to 6;
   R1 is selected from the group consisting of hydrogen, a saturated or unsaturated ($C_1$-$C_{12}$)-alkyl group, a ($C_1$-$C_{12}$)-alkyl group substituted by a halogen atom, a hydroxy-($C_2$-$C_{12}$)-alkyl group, an amino-($C_1$-$C_{12}$)-alkyl group, a substituted or unsubstituted phenyl group and a substituted or unsubstituted benzyl group;
   R2, R4, R5 and R7 may be identical or different and, independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a ($C_1$-$C_{12}$)-thioalkyl group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group, a substituted or unsubstituted naphthyl group and a substituted or unsubstituted heteroaryl group;

or if Y and Z are C—R5 and C—R7, the radical groups R5 and R7, together with the remaining molecule, can form a heterocyclic or carbocyclic, saturated or unsaturated, substituted or unsubstituted ring system;

or if X and Y are C—R4 and C—R5, the radical groups R4 and R5, together with the remaining molecule, can form a heterocyclic or carbocyclic, saturated or unsaturated, substituted or unsubstituted ring system;

R3 and R6 may be identical or different and, independently of one another, are selected from the group consisting of a saturated or unsaturated ($C_1$-$C_{12}$)-alkyl group, a ($C_1$-$C_{12}$)-alkyl group substituted by a halogen atom (F, Cl, Br, I), a hydroxy-($C_2$-$C_{12}$)-alkyl group, an amino-($C_1$-$C_{12}$)-alkyl group, a substituted or unsubstituted phenyl group and a substituted or unsubstituted benzyl group:

Q+ represents a quaternary monoalkylammonium, dialkylammonium or trialkylammonium group, where the alkylgroups may be identical or different and, independently of one another, are a saturated or unsaturated ($C_1$-$C_{12}$)-alkyl group;

with the proviso that when Q+ represents a tri($C_1$-$C_4$) alkylammonium group, and X is sulfur and Y is nitrogen or a CH group, Z is not a C—R5 residue with R5 representing hydrogen, a halogen atom, a nitro group or an alkylgroup;

or Q+ represents a quaternary monoarylammonium, diarylammonium or triarylammonium group, where the arylgroups may be identical or different and, independently of one another, are an unsubstituted or substituted phenylgroup;

or Q+ represents a quaternary alkylarylammonium group, where the alkylgroups may be identical or different and, independently of one another, are a saturated or unsaturated ($C_1$-$C_{12}$)-alkyl group, and the arylgroups may be identical or different and, independently of one another, are an unsubstituted or substituted phenylgroup;

the anion An- is an organic or inorganic acid anion.

3. An agent for the simultaneous lightening and coloring of keratin fibers, comprising at least one oxidizing agent, characterized by comprising at least one azodye of the general formula (I);

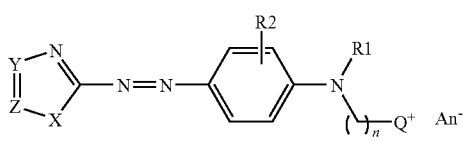

(I)

wherein
X is selected from the group consisting of oxygen, sulfur, N—R3 and C—R4;

Y is selected from the group consisting of C—R5, nitrogen, N—R6, sulfur and oxygen;

Z is C—R7 or nitrogen;

with the proviso that the heterocycle of the formula (I) comprises at least two and at most three heteroatoms, where the heterocycle has at most one sulfur atom or one oxygen atom;

n is an integer from 1 to 6;

R1 is selected from the group consisting of hydrogen, a saturated or unsaturated ($C_1$-$C_{12}$)-alkyl group, a ($C_1$-$C_{12}$)-alkyl group substituted by a halogen atom, a hydroxy-($C_2$-$C_{12}$)-alkyl group, an amino-($C_1$-$C_{12}$)-alkyl group, a substituted or unsubstituted phenyl group and a substituted or unsubstituted benzyl group;

R2, R4, R5 and R7 may be identical or different and, independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group a hydroxy-($C_1$-$C_{12}$)-alkyl group, a ($C_1$-$C_{12}$)-alkoxy group, a ($C_1$-$C_{12}$)-thioalkyl group, a cyano group, a nitro group, an amino group, a ($C_1$-$C_{12}$)-alkylamino group, a ($C_1$-$C_2$)-dialkylamino group, a carboxylic acid group, a C(O)O—($C_1$-$C_{12}$)-alkyl group, a substituted or unsubstituted C(O)O-phenyl group, a substituted or unsubstituted phenyl group, a substituted or unsubstituted naphthyl group and a substituted or unsubstituted heteroaryl group; or if Y and Z are C—R5 and C—R7, the radical groups R5 and R7, together with the remaining molecule, can form a heterocyclic or carbocyclic, saturated or unsaturated, substituted or unsubstituted ring system;

or if X and Y are C—R4 and C—R5, the radical groups R4 and R5, together with the remaining molecule, can form a heterocyclic or carbocyclic, saturated or unsaturated, substituted or unsubstituted ring system;

R3 and R6 may be identical or different and, independently of one another, are selected from the group consisting of a saturated or unsaturated ($C_1$-$C_{12}$)-alkyl group, a ($C_1$-$C_{12}$)-alkyl group substituted by a halogen atom (F, Cl, Br, I), a hydroxy-($C_2$-$C_{12}$)-alkyl group, an amino-($C_1$-$C_{12}$)-alkyl group, a substituted or unsubstituted phenyl group and a substituted or unsubstituted benzyl group;

Q+ represents a quaternary trialkylammonium group, where the alkylgroups may be identical or different and, independently of one another, are a saturated or unsaturated ($C_1$-$C_{12}$)-alkyl group;

with the proviso that when Q+ represents a tri($C_1$-$C_4$) alkylammonium group, and X is sulfur and Y is nitrogen or a CH group, Z is not a C—R5 residue with R5 representing hydrogen, a halogen atom, a nitro group or an alkylgroup;

the anion An— is an organic or inorganic acid anion.

4. An agent for oxidative coloring of keratin fibers based on at least one oxidation dye precursor, comprising at least one azodye of the general formula (I);

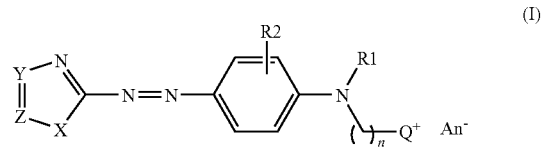

(I)

wherein
- X is selected from the group consisting of oxygen, sulfur, N—R3 and C—R4;
- Y is selected from the group consisting of C—R5, nitrogen, N—R6, sulfur and oxygen;
- Z is C—R7 or nitrogen;
- with the proviso that the heterocycle of the formula (I) comprises at least two and at most three heteroatoms, where the heterocycle has at most one sulfur atom or one oxygen atom;
- n is an integer from 1 to 6;
- R1 is selected from the group consisting of hydrogen, a saturated or unsaturated (C1-$C_{12}$)-alkyl group, a ($C_1$-$C_{12}$)-alkyl group substituted by a halogen atom, a hydroxy-($C_2$-$C_{12}$)-alkyl group, an amino-($C_1$-$C_{12}$)-alkyl group, a substituted or unsubstituted phenyl group and a substituted or unsubstituted benzyl group;
- R2, R4, R5 and R7 may be identical or different and, independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a ($C_1$-$C_{12}$)-thioalkyl group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group, a substituted or unsubstituted naphthyl group and a substituted or unsubstituted heteroaryl group;
- or if Y and Z are C—R5 and C—R7, the radical groups R5 and R7, together with the remaining molecule, can form a heterocyclic or carbocyclic, saturated or unsaturated, substituted or unsubstituted ring system;
- or if X and Y are C—R4 and C—R5, the radical groups R4 and R5, together with the remaining molecule, can form a heterocyclic or carbocyclic, saturated or unsaturated, substituted or unsubstituted ring system;
- R3 and R6 may be identical or different and, independently of one another, are selected from the group consisting of a saturated or unsaturated ($C_1$-$C_{12}$)-alkyl group, a ($C_1$-$C_{12}$)-alkyl group substituted by a halogen atom (F, Cl, Br, I), a hydroxy-($C_2$-$C_{12}$)-alkyl group, an amino-($C_1$-$C_{12}$)-alkyl group, a substituted or unsubstituted phenyl group and a substituted or unsubstituted benzyl group;
- Q+ represents a quaternary trialkylammonium group, where the alkylgroups may be identical or different and, independently of one another, are a saturated or unsaturated ($C_1$-$C_{12}$)-alkyl group;
- with the proviso that when Q+ represents a tri($C_1$-$C_4$) alkylammonium group, and X is sulfur and Y is nitrogen or a CH group, Z is not a C—R5 residue with R5 representing hydrogen, a halogen atom, a nitro group or an alkylgroup; the anion An- is an organic or inorganic acid anion.

5. A composition according to claim 1, wherein in the formula (I)$Q^+$ represents a quaternary trialkylammonium group, where the alkylgroups may be identical or different and, independently of one another, are a saturated or unsaturated ($C_1$-$C_{12}$)-alkyl group;
with the proviso that when Q+ represents a tri($C_1$-$C_4$) alkylammonium group, and X is sulfur and Y is nitrogen or a CH group, Z is not a C—R5 residue with R5 representing hydrogen, a halogen atom, a nitro group or an alkylgroup;
the alkylgroups may be identical or different and, independently of one another, being a saturated or unsaturated ($C_1$-$C_{12}$)-alkyl group and the aryl group being a substituted or unsubstituted phenyl group.

6. A method according to claim 2, wherein in the formula (I) $Q^+$ represents a quaternary trialkylammonium group, where the alkylgroups may be identical or different and, independently of one another, are a saturated or unsaturated ($C_1$-$C_{12}$)-alkyl group;
with the proviso that when Q+ represents a tri($C_1$-$C_4$) alkylammonium group, and X is sulfur and Y is nitrogen or a CH group, Z is not a C—R5 residue with R5 representing hydrogen, a halogen atom, a nitro group or an alkylgroup;
the alkylgroups may be identical or different and, independently of one another, being a saturated or unsaturated ($C_1$-$C_{12}$)-alkyl group and the aryl group being a substituted or unsubstituted phenyl group.

7. A composition according to claim 1, wherein the cationic azodye of the formula (I) is chosen from 2-[{4-[(4,5-dimethyl-1,3-thiazol-2-yl)diazenyl]phenyl}(ethyl)amino]-N,N,N-trimethylethanaminium bromide; 2-[{4-[(4,5-dimethyl-1,3-thiazol-2-yl)diazenyl]-3-methylphenyl}(ethyl)-amino]-N,N,N-trimethylethanaminium bromide; 2-[{3-chloro-4-[(4,5-dimethyl-1,3-thiazol-2-yl)diazenyl]phenyl}(ethyl)amino]-N,N,N-trimethylethanaminium bromide; 2-[{4-[(4-methyl-1,3-thiazol-2-yl)diazenyl]phenyl}(ethyl)amino]-N,N,N-trimethylethanaminium bromide;

2-[{4-[(4-methyl-1,3-thiazol-2-yl)diazenyl]-3-methylphenyl}(ethyl)amino]-N,N,N-trimethylethanaminium bromide; 2-[{3-chloro-4-[(4-methyl-1,3-thiazol-2-yl)diazenyl]phenyl}(ethyl)amino]-N,N,N-trimethylethanaminium bromide; 2-[{4-[1,3-benzothiazol-2-yldiazenyl]phenyl}(ethyl)amino]-N,N,N-trimethylethanaminium bromide; 2-(ethyl{4-[(6-nitro-1,3-benzothiazol-2-yl)diazenyl]phenyl}amino)-N,N,N-trimethylethanaminium bromide; 2-[{4-[(5,6-dinitro-1,3-benzothiazol-2-yl)diazenyl]phenyl}(ethyl)amino]-N,N,N-trimethylethanaminium bromide; 2-[{4-[(4,6-dinitro-1,3-benzothiazol-2-yl)diazenyl]phenyl}(ethyl)amino]-N,N,N-trimethylethanaminium bromide; 2-(ethyl{4-[(4-methyl-6-nitro-1,3-benzothiazol-2-yl)diazenyl]phenyl}amino)-N,N,N-trimethylethanaminium bromide; 2-[{4-[(4-chloro-6-nitro-1,3-benzothiazol-2-yl)diazenyl]-phenyl}(ethyl)amino]-N,N,N-trimethylethanaminium bromide; 2-(ethyl{4-[1H-[1,3]thiazolo[5,4-f]indazol-6-yldiazenyl]phenyl}amino)-N,N,N-trimethylethanaminium bromide; 2-[{4-[(5-chloro[1,3]thiazolo[5,4-b]pyridin-2-yl)diazenyl]phenyl}(ethyl)amino]-N,N,N-trimethylethanaminium bromide; 2-[{4-[(5-methoxy[1,3 ]thiazolo[5,4-b]pyridin-2-yl)diazenyl]-phenyl}(ethyl)amino]-N,N,N-trimethylethanaminium bromide; N,N-diethyl-2-(ethyl{4-[1,3-thiazol-2-yldiazenyl]phenyl}amino)-N-methylethanaminium bromide;

N-[2-(ethyl{4-[1,3-thiazol-2-yldiazenyl]phenyl}amino) ethyl]-N,N-dimethylbenzenaminium bromide; 2-(ethyl{4-[1,2,4-thiadiazol-5-yldiazenyl]phenyl}amino)-N,N,N-trimethylethanaminium bromide; 2-(ethyl{4-[(3-phenyl-1,2,4-thiadiazol-5-yl)diazenyl]phenyl }amino)-N,N,N-trimethylethanaminium bromide; 2-[{4-[(3-chloro-1,2,4-thiadiazol-5-yl)diazenyl]phenyl}(ethyl)amino]-N,N,N-trimethylethanaminium bromide; 2-(ethyl{4-[1H-1,2,4-triazol-5-yldiazenyl]phenyl}-amino)-N,N,N-trimethylethanaminium bromide; 1-[2-(ethyl{4-[(1- methyl-1H-imidazol-2-yl)diazenyl]-phenyl}amino)ethyl]-N,N,N-trimethylethanaminium bromide;

1-[2-(ethyl{3-methyl-4-[(1-methyl-1H-imidazol-2-yl)diazenyl]phenyl}amino)ethyl]-N,N,N-trimethylethanaminium bromide and 1-{2-[{3-chloro-4-[(1-methyl-1H-imidazol-2-yl)diazenyl]phenyl}(ethyl)amino]ethyl}-N,N,N-trimethylethanaminium bromide.

8. A method according to claim 2, wherein the cationic azodye of the formula (I) is chosen from 2-[{4-[(4,5-dimethyl-1,3-thiazol-2-yl)diazenyl]phenyl}(ethyl)amino]-N,N,N-trimethylethanaminium bromide; 2-[{4-[(4,5-dimethyl-1,3-thiazol-2-yl)diazenyl]-3-methylphenyl}(ethyl)-amino]-N,N,N-trimethylethanaminium bromide; 2-[{3-chloro-4-[(4,5-dimethyl-1,3-thiazol-2-yl)diazenyl]phenyl}(ethyl)amino]-N,N,N-trimethylethanaminium bromide; 2-[{4-[(4-methyl-1,3-thiazol-2-yl)diazenyl]phenyl}(ethyl)amino]-N,N,N-trimethylethanaminium bromide;

2-[{4-[(4-methyl-1,3-thiazol-2-yl)diazenyl]-3-methylphenyl}(ethyl)amino]-N,N,N-trimethylethanaminium bromide; 2-[{3-chloro-4-[(4-methyl-1,3-thiazol-2-yl)diazenyl]phenyl}(ethyl)amino]-N,N,N-trimethylethanaminium bromide; 2-[{4-[1,3-benzothiazol-2-yldiazenyl]phenyl}(ethyl)amino]-N,N,N-trimethylethanaminium bromide; 2-(ethyl{4-[(6-nitro-1,3-benzothiazol-2-yl)diazenyl]phenyl}amino)-N,N,N-trimethylethanaminium bromide; 2-[{4-[(5,6-dinitro-1,3-benzothiazol-2-yl)diazenyl]phenyl}(ethyl)amino]-N,N,N-trimethylethanaminium bromide; 2-[{4-[(4,6-dinitro-1,3-benzothiazol-2-yl)diazenyl]phenyl}(ethyl)amino]-N,N,N-trimethylethanaminium bromide; 2-(ethyl{4-[(4-methyl-6-nitro-1,3-benzothiazol-2-yl)diazenyl]phenyl}amino)-N,N,N-trimethylethanaminium bromide; 2-[{4-[(4-chloro-6-nitro-1,3-benzothiazol-2-yl)diazenyl]-phenyl}(ethyl)amino]-N,N,N-trimethylethanaminium bromide; 2-(ethyl{4-[1H-[1,3]thiazolo [5,4-f]indazol-6-yldiazenyl]phenyl}amino)-N,N,N-trimethylethanaminium bromide; 2-[{4-[(5-chloro[1,3]thiazolo[5,4-b]pyridin-2-yl)diazenyl]phenyl}(ethyl)amino]-N,N,N-trimethylethanaminium bromide; 2-[{4-[(5-methoxy[1,3]thiazolo[5,4-b]pyridin-2-yl)diazenyl]-phenyl}(ethyl)amino]-N,N,N-trimethylethanaminium bromide; N,N-diethyl-2-(ethyl{4-[1,3-thiazol-2-yldiazenyl]phenyl}amino)-N-methylethanaminium bromide;

N-[2-(ethyl{4-[1,3-thiazol-2-yldiazenyl]phenyl}amino)ethyl]-N,N-dimethylbenzenaminium bromide; 2-(ethyl{4-[1,2,4-thiadiazol-5-yldiazenyl]phenyl}amino)-N,N,N-trimethylethanaminium bromide; 2-(ethyl{4-[(3-phenyl-1,2,4-thiadiazol-5-yl)diazenyl]phenyl }amino)-N,N,N-trimethylethanaminium bromide; 2-[{4-[(3-chloro-1,2,4-thiadiazol-5-yl)diazenyl]phenyl}(ethyl)amino]-N,N,N-trimethylethanaminium bromide; 2-(ethyl{4-[1H-1,2,4-triazol-5-yldiazenyl]phenyl}-amino)-N,N,N-trimethylethanaminium bromide; 1-[2-(ethyl{4-[(1-methyl-1H-imidazol-2-yl)diazenyl]-phenyl}amino)ethyl]-N,N,N-trimethylethanaminium bromide; 1-[2-(ethyl{3-methyl-4-[(1-methyl-1H-imidazol-2-yl)diazenyl]phenyl}amino)ethyl]-N,N,N-trimethylethanaminium bromide and 1-{2-[{3-chloro-4-[(1-methyl-1H-imidazol-2-yl)diazenyl]phenyl}(ethyl)amino]ethyl}-N,N,N-trimethylethanaminium bromide.

9. A composition as claimed in claim 1, wherein the composition comprises from 0.01 to 10% by weight of said cationic azodye of said formula (I).

10. A composition as claimed in claim 1, wherein the composition is a hair colorant composition.

\* \* \* \* \*